(12) United States Patent
Phillips

(10) Patent No.: US 8,584,518 B2
(45) Date of Patent: Nov. 19, 2013

(54) GAS TRAP FOR DRILLING MUD HAVING QUICK-RELEASE SEPARABLE LOWER SECTION

(75) Inventor: Terence D. Phillips, Calgary (CA)

(73) Assignee: Rigsat Communications Inc., Calgary (CA)

( * ) Notice: Subject to any disclaimer, the term of this patent is extended or adjusted under 35 U.S.C. 154(b) by 426 days.

(21) Appl. No.: 12/827,334

(22) Filed: Jun. 30, 2010

(65) Prior Publication Data

US 2012/0000278 A1 Jan. 5, 2012

(51) Int. Cl.
*E21B 47/00* (2012.01)

(52) U.S. Cl.
USPC ............................................. 73/152.04

(58) Field of Classification Search
USPC .......... 220/328, 327, 315; 366/264, 249, 250, 366/251, 331, 329.1; 403/318, 319, 355, 403/455; 73/152.04, 19.09, 23.2, 61.45, 73/61.41, 19.01; 175/206, 207, 209; 95/260
See application file for complete search history.

(56) References Cited

U.S. PATENT DOCUMENTS

| | | | | |
|---|---|---|---|---|
| 2,704,658 A | * | 3/1955 | Gordon | 366/329.1 |
| 4,358,298 A | * | 11/1982 | Ratcliff | 96/189 |
| 5,199,509 A | | 4/1993 | Wright et al. | 175/50 |
| 5,648,603 A | | 7/1997 | Hanson | 73/152.05 |
| 6,315,147 B1 | * | 11/2001 | Bachmeier | 220/325 |
| 6,389,878 B1 | | 5/2002 | Zamfes | 73/19.09 |
| 8,091,726 B2 | * | 1/2012 | Bradshaw et al. | 220/315 |
| 2009/0077936 A1 | | 1/2009 | Sterner | 55/422 |

* cited by examiner

*Primary Examiner* — Peter MacChiarolo
*Assistant Examiner* — Tamiko Bellamy
(74) *Attorney, Agent, or Firm* — George A. Seaby

(57) ABSTRACT

A gas trap apparatus for liberating gas from drilling mud and collecting such gas for analysis. A motor is connected to a rotatable vertical shaft having beater bars thereon, which when the shaft is immersed in drilling mud and rotate, stirs such mud to liberate gas entrained therein. The gas trap is characterized in having a top member and a bottom member which surrounds the vertical shaft and which is releasably secured to the top member thereof by a quick release mechanism which facilitates rapid detachment of the bottom member from the top member to permit quick access said vertical shaft and beater bars thereon for replacement or servicing. The vertical shaft may further likewise be provided with a quick-release means to allow quick release of the shaft from the motor for easy replacement and servicing of same.

6 Claims, 8 Drawing Sheets

GAS TRAP FOR DRILLING MUD HAVING QUICK-RELEASE SEPARABLE LOWER SECTION

FIELD OF THE INVENTION

The invention relates to a gas trap apparatus for mud logging when drilling for hydrocarbons.

BACKGROUND OF THE INVENTION AND DESCRIPTION OF THE PRIOR ART

"Drilling mud" is a generic term for a fluid containing dispersed solids which is used in the drilling of wells. Drilling mud, comprising various chemical compounds, is pumped down the drill string during the drilling of a well to assist, among other things, in cooling the drill bit, minimizing corrosion of drill pipe, pressurizing the well against hydrostatic head when the drill string enters a pressurized formation, and further to carry drill chips away from the drill bit, which then become suspended in such drilling mud. The drilling mud flows back to surface, typically in the annulus between the drill string and the well casing.

When a hydrocarbon-containing strata is encountered during drilling of a well, a certain amount of the gas containing hydrocarbons from the strata will be entrained in the drilling mud and thus be carried to the surface by the drilling operation. Thus any entrained gas, when extracted from the drilling mud, can be analyzed and used to determine the presence of hydrocarbon and the likely "quality" of the hydrocarbon-bearing formation (ie provide an estimate of the quantum of hydrocarbon in the strata being drilled through) at the depth of the well at which such hydrocarbon-bearing strata existed.

The above procedure is known as "mud logging" and is a critical process in the drilling of wells for determining if the drilled well has successfully encountered a "rich" hydrocarbon-containing formation, the "quality" of the formation, and the depth at which such hydrocarbon-bearing formation was encountered.

Gas trap devices for facilitating the liberation of gases from drilling mud and collecting such gases during drilling for subsequent analysis in mud-logging operations are well known in the mud-logging industry.

Such prior art gas trap devices are typically mounted on "mud tanks", and serve to: (i) agitate the mud collected in such tanks from a well being drilled in order to liberate any gas entrained therein; and (ii) collect such liberated gas from the agitated mud and direct such collected gas to gas detection and analysis equipment.

One such gas trap device 10 is disclosed in U.S. Pat. No. 5,199,509 entitled "Controlled Gas Trap System", assigned to Texaco Inc. Such gas trap device 10, as shown in FIG. 1 thereof, possesses a cylindrical trap body 12 closed at its upper end by plate 14 and at its lower end by a plate 16 having a central annular aperture 18 which is co-axial with the housing 12, with plates 16 and 20 defining a mixing chamber 24 therebetween. A constant speed motor 26 is mounted co-axially on the top plate 14, and a downwardly-extending vertical shaft 30 of the motor extends downwardly into the interior of the housing 12. An agitator 42 is connected to the bottom of the shaft 30 and lies in the mixing chamber 24. Agitator 42 possesses a series of legs 44, 46, 48 ("beater bars") which when rotated by shaft 30 serve to agitate drilling mud to thereby liberate any entrained gas, which is collected via sample line 34 for analysis.

Another similar prior art gas trap is that taught in U.S. Pat. No. 5,648,603, likewise assigned to Texaco Inc., which discloses a similar gas trap 11 having a similar plurality of legs 18, which collects liberated gas from agitated drilling mud in head space 21, with the added feature of providing a standard gas from a standard gas source 27 (a pressurized tank). The flow of standardized gas is calibrated, to assist in error correction with regard to the sampled (liberated) gas stream.

U.S. Pat. No. 6,389,878 teaches a similar type of gas trap 1, possessing a modification wherein the shaft 43 extending downwardly from motor 41 is hollow, with radially-extending tubes 44 extending radially outwardly therefrom, which serve to inject "stripping" air into the drilling mud, which air is drawn (along with gas entrained in the mud) upwardly within the gas trap for subsequent collection via tube 20 and thereafter compositional analysis. Significantly, US '878 expressly teaches that the gas trap 1 is comprised of an upper and lower canisters 13, 12, respectively, each of which is a truncated right circular cone. The truncated open end 19 of the upper canister 13 is smaller than the truncated open end 15 of the lower canister 12 so that it is partially insertable into lower canister 12. The upper and lower canisters 13, 12 are sealably joined at their connective interface 23. No means of quick release of one canister from the other is taught or suggested.

US Patent Publication 200910077936 teaches a similar gas trap, with the added feature that such gas trap is vertically variably positionable. Significantly, the container 16 which contains the stirrer 32, appears to be a unitary construction, with no disclosure of means to access the stirrer 32 in the event replacement is required.

Problematically, due the drilling mud containing significant abrasives, not the least of which is drill chips entrained therein from drilling operations, as well as having (and being designed to entrain therewithin) suspended solid particles, such drilling mud and abrasive particles therein causes serious and substantial wear to rotating outwardly-radially extending "beater bars" on the agitator shaft, frequently resulting (depending on the speed of rotation of the shaft and the amount of abrasives contained in the drilling mud) in breakage and/or substantial material loss of the beater bars, all of which result in ineffective or reduced effective operation of the agitation of the drilling mud and thus the gas trap, requiring servicing of or replacement of the shaft and/or one or more beater bars of the gas trap.

Thus a significant disadvantage of each of the prior art gas traps and their designs is that the container (or plates) which surround the shaft make replacement or access to the shaft difficult or impossible.

Similarly, prior art gas traps sold by RigSat Communications Inc. (the within application assigned to such entity) possessed a bottom member which surrounded the shaft and beater bars, which was releasably secured to a top section on which the motor was mounted by means of threaded bolts and mating threaded apertures. Although such design, being of a two part construction, allowed access to the shaft upon removal of the threaded bolts, such was time consuming and often resulted in loss of bolts within the mud tanks upon which the gas traps were mounted.

Accordingly, a real need exists in the prior art for a gas trap of two-part construction, which allows ready and easy access to beater bars to adequately service or replace such shafts and/or beater bars, in order to reduce maintenance costs (and "down" time) of existing gas traps in mud logging operations.

SUMMARY OF THE INVENTION

In order to overcome the aforementioned disadvantages of existing gas traps and provide a gas trap for use in mud logging operations which allows rapid access to mixing components for servicing and/or replacement thereof, in a first broad embodiment the gas trap apparatus of the present invention comprises:

an elongate, vertically-downwardly extending shaft, having stirring means thereon to stimulate and cause circulation of drilling mud when extended into and rotated within drilling mud;

motor means for rotating said downwardly-extending shaft, a top member, situated below said motor means, said shaft passing vertically downwardly through and extending below said top member, having a gas collection port therein for allowing gas liberated from said drilling mud to be collected and withdrawn for analysis;

a bottom member, extending around said shaft; and quick-release coupling means, releasably coupling said upper portion of said bottom member to said lower portion of said top member, to permit rapid detachment of said bottom member from said top member to thereby allow access to said downwardly-extending shaft and stirring means when same need servicing or replacement.

In a further (optional) embodiment, the shaft itself has quick-release coupling means thereon to permit quick release of said shaft and/or stirring means thereon, to thereby facilitate rapid replacement of said shaft and/or stirring means. In a particular embodiment, the gas trap apparatus has coupling means situated on the beater bars, which permit quick release of said beater bars from said shaft, to thereby facilitate rapid replacement of said beater bars. In another embodiment, the shaft has quick release coupling means which engage the motor and shaft, to permit quick release of a used shaft and beater bars, and quick coupling of a new shaft and beater bars to the motor. Such quick-release coupling means can be of any type, but in a preferred embodiment is a "pin and groove" arrangement, whereby a protruding pin or other protuberance releasably engages a corresponding groove in the mating component, to provide such quick-release coupling of the two components.

In a particular embodiment of the invention, the quick release coupling means on the gas trap itself preferably comprises a "U" shaped member, the elongate two arms of which are separated by a distance to permit insertion of such arms into respective apertures situated on the periphery of each of the top section and bottom section of the gas trap. Such apertures, when the elongate arms of such "U" shaped member are inserted respectively into such apertures, serve to frictionally engage the elongate arms and lock the bottom member of the gas trap to the top member. When access is desired to the rotating shaft of the gas trap for servicing or replacement thereof, the "U" shaped member may be grasped by its base and pulled in a direction perpendicular to the axis of the gas trap, which thereby withdraws the elongate arms from the apertures, thereby releasing the bottom member from the top member and allowing access to the rotating shaft which is otherwise, in the operative position, surrounded by such bottom member.

In an alternative embodiment of the quick-release coupling means, such quick-release coupling means comprises at least one manually-actuated clip (preferably a plurality of clip members) which releasably join the bottom member to the top member and which may be easily removed or released to permit detachment of said upper portion of said bottom section from said lower portion of said top section. In a refinement of such alternative embodiment, the at least one manually-actuated clip comprises:

(i) a plurality of bale members, pivotally secured to said lower portion of said top section about a periphery thereof, and (ii) a plurality of protruding detent members, extending from said upper portion of said bottom member, engagable with said bale members to releasably secure said bottom member to said top member.

Alternatively, such embodiment may comprise:

(i) a plurality of bale members, pivotally secured to said upper portion of said bottom section about a periphery thereof, and (ii) a plurality of protuberances, extending from said bottom portion of said top member, engagable with said bale members to releasably secure said bottom member to said top member.

In a further alternative embodiment of the quick-release coupling means, such quick-release coupling means comprises segmented rim means on each of said lower portion of said top member, and said upper portion of said bottom member, to permit locked engagement thereof, wherein said upper portion of said bottom member, when inserted into and rotated in a first direction about a vertical axis relative to said top member, becomes secured to said top member due to engagement of said respective segmented rim means, and when said bottom member is rotated in an opposite direction about said vertical axis said bottom member may be removed from engagement with said top member.

BRIEF DESCRIPTION OF THE DRAWINGS

Further advantages and permutations and combinations of the invention will now appear from the above and from the following detailed description of the various particular embodiments of the invention taken together with the accompanying drawings, each of which are intended to be non-limiting, in which:

FIG. 6b is an bottom perspective "exploded" view of the gas trap of the present invention, showing a variation of the quick release means shown in FIG. 6a.

DETAILED DESCRIPTION OF PREFERRED EMBODIMENTS

Figure 1:
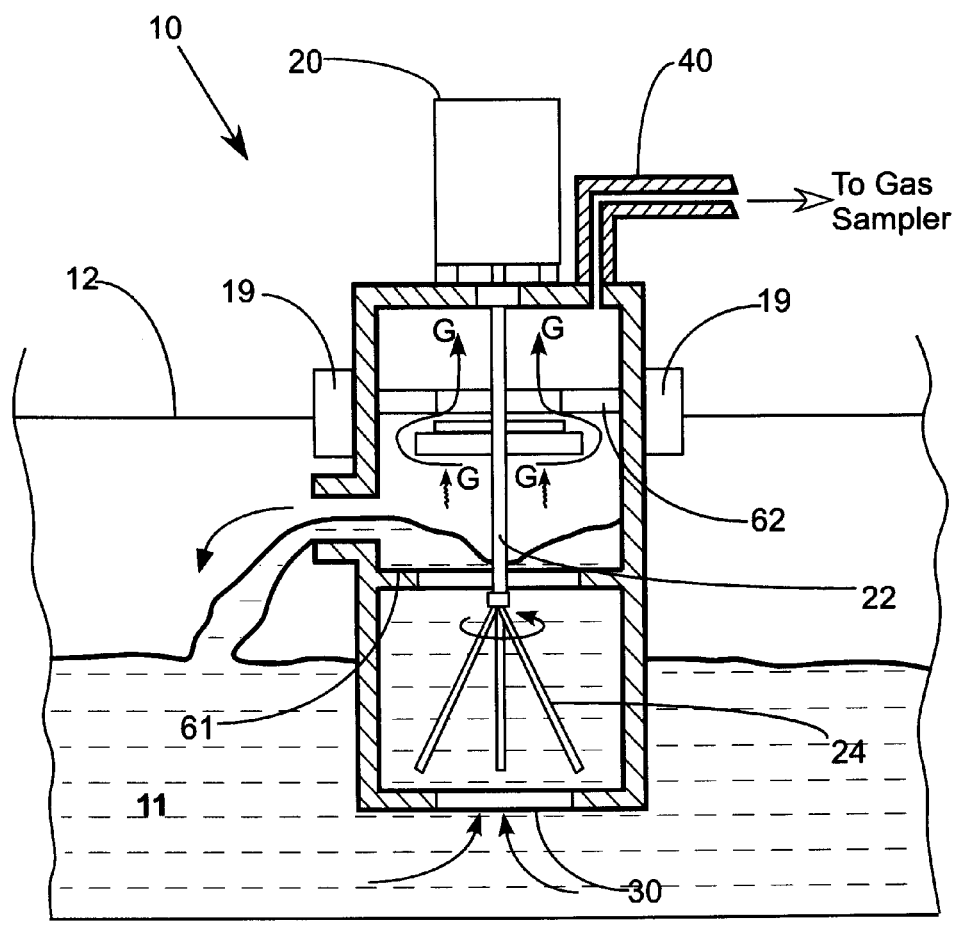
FIG. 1 is a cross-sectional view of a gas trap of the prior art, shown mounted on the side of a mud-tank.

FIG. 1 shows a gas trap 10 of the prior art for stimulating release of any gas "G" which is entrained in drilling mud 11.

FIG. 1 shows the manner of operation of a prior art gas trap 10, when such gas trap 10 is attached via attachment means 14 (which may be any type of attachment, such as by bolting, or simply hanging) to the side of a mud tank 12.

In operation, motor means 20 turns rotating shaft 22, which in turn rotates "beater bars" 24 which agitate drilling mud 11 in gas trap 10. Drilling mud 11 flows into mud entry aperture 30 in the bottom of gas trap 10 (see arrows directed into aperture 30), and the rotation of beater bars 24 releases gas "G". Entrained gas "G" flows upwardly in gas trap 10, and is drawn by means of vacuum pressure or the like through gas collection port 40 on the gas trap 10 to a gas sampler device (not shown). Drilling mud 11 (with entrained gas "G" removed therefrom) then exits gas trap 10 via mud exit aperture 50, whereupon such drilling mud 11 returns to mud tank 12, as shown in FIG. 1.

Disadvantageously, as may be seen from FIG. 1, gas trap 10 of the prior art typically comprised of a one-piece construction, further often having integral plates 61, 62 therein, which made disassembly of such prior art gas trap for the purposes of servicing worn parts therein extremely difficult, if not impossible.

Specifically, due to rotation of beater bars 24 within drilling mud 11, such beater bars 24 often became seriously worn, often leading to breakage thereof, which in either case resulted in failure of the gas trap 10 to adequately agitate drilling mud 11 to release entrained gas "G" therein.

Figure 2:
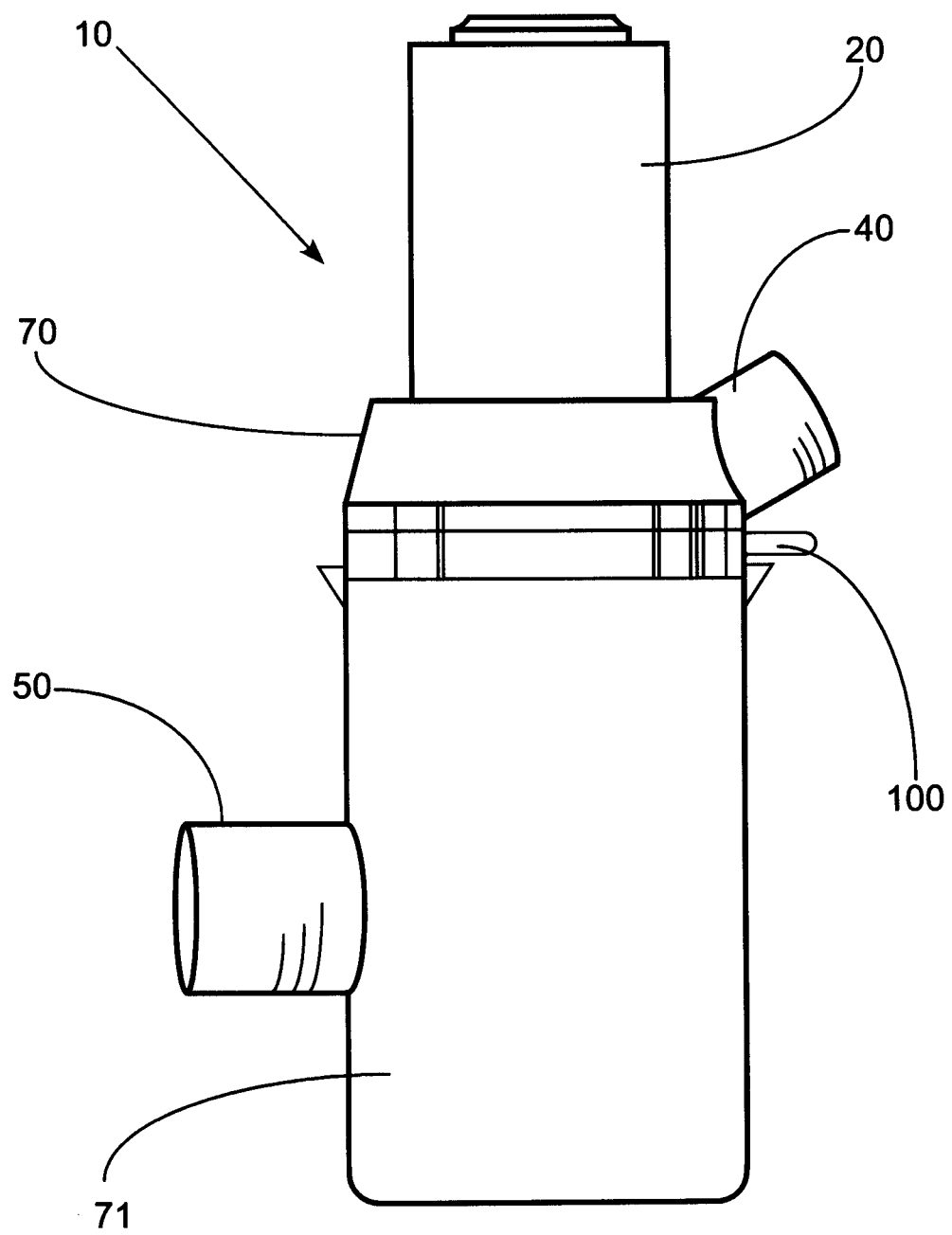
FIG. 2 is a side view of a preferred embodiment of the gas trap of the present invention, showing the top member and bottom member releasably secured to each other using a quick-release mechanism of the present invention.

FIG. 2 shows a side view of the gas trap 10 of the present invention. Such gas trap 10 is comprised of a minimum two-piece construction, having a top member/section 70 and a bottom member/section 71, which are separable. A gas collection port 40 is located in top member 70, and a mud exit aperture 50 is located in bottom member 71. A motor 20 is situated on top member 70. A quick release mechanism 100, as further described below, is provided, to allow quick release of bottom member 71 from top member 70.

Figure 3:
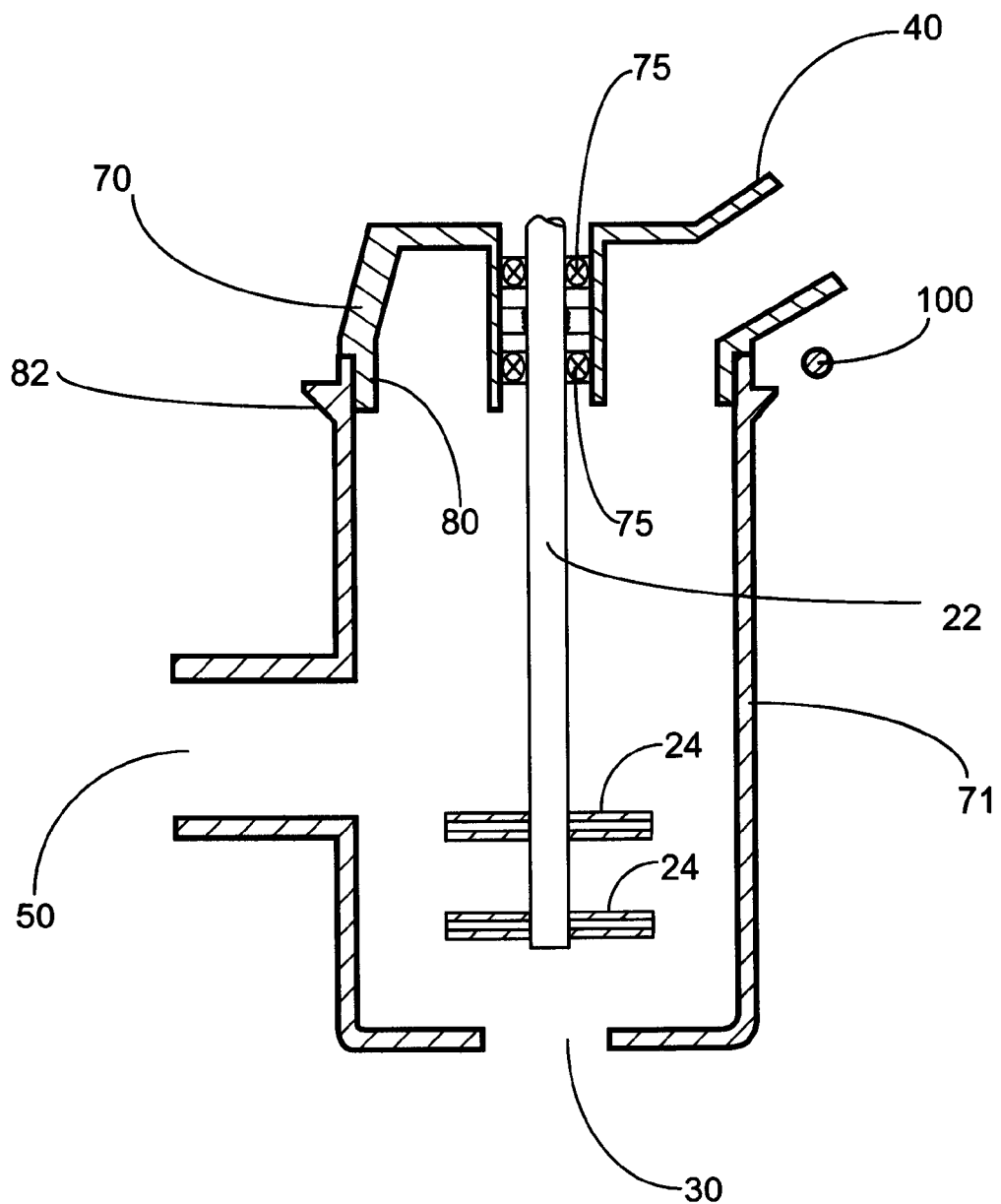
FIG. 3. is a cross-sectional view of the gas trap of FIG. 2 taken along plane B-B, with the motor omitted.

As may be seen from FIG. 3, such being a cross-section through the gas trap 10 of the present invention shown in FIG. 2, rotating shaft 22 extends through top member 70 vertically downwardly into bottom member 71. Bearings 75 may be provided in top member 70, to centrally retain and permit rotation of shaft 22 in top member 70. Beater bars 24 are affixed to shaft 22 at a distal end of shaft 22, which when shaft 22 is rotated, cause agitation of drilling mud 11 and release of entrained gas "G" therewithin. Flange 80, forming a bottom portion of top member 70, extends downwardly so as to co-axially fit within and matingly engage upper portion 82 on bottom member 71 of gas trap 10. Mud entry aperture 30 is located in bottom member 71.

Figure 5:
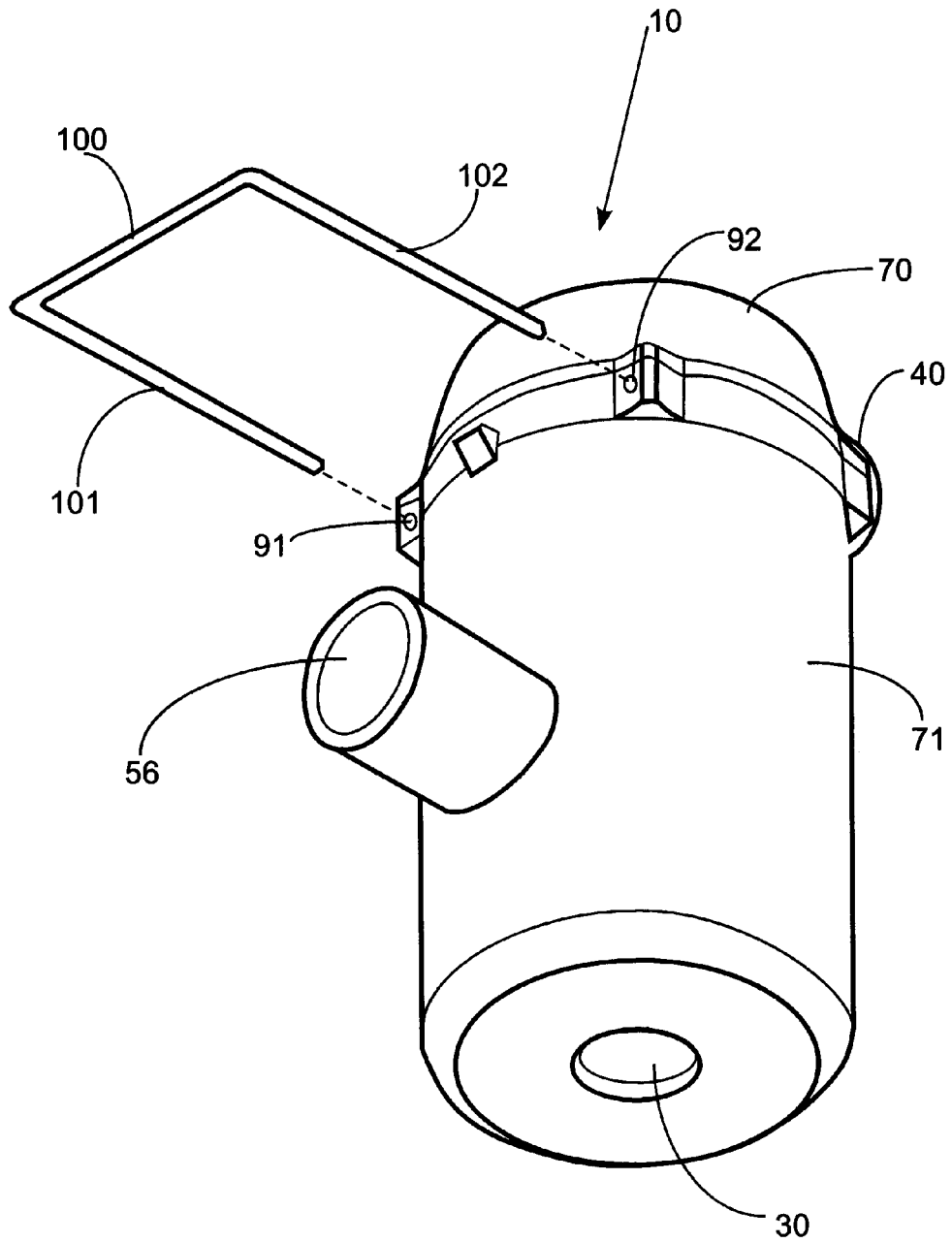
FIG. 5 is a similar bottom perspective "non-exploded" view of the gas trap shown in FIG. 4, with the "U" shaped quick release member about to be inserted.

FIG. 5 shows a bottom perspective (partially "exploded") view of the gas trap 10 of the present invention, clearly showing the operation of a first embodiment of a quick release means 100, which quick release means 100 may be manually pulled radially outwardly by a service technician from the gas trap 10, to allow immediate disengagement between top member 70 and bottom member 71 so as to permit removal of the bottom member 71 from the gas trap 10 so as to thereby permit access to the shaft 22 and beater bars 24 for servicing and/or repair.

Figure 4:
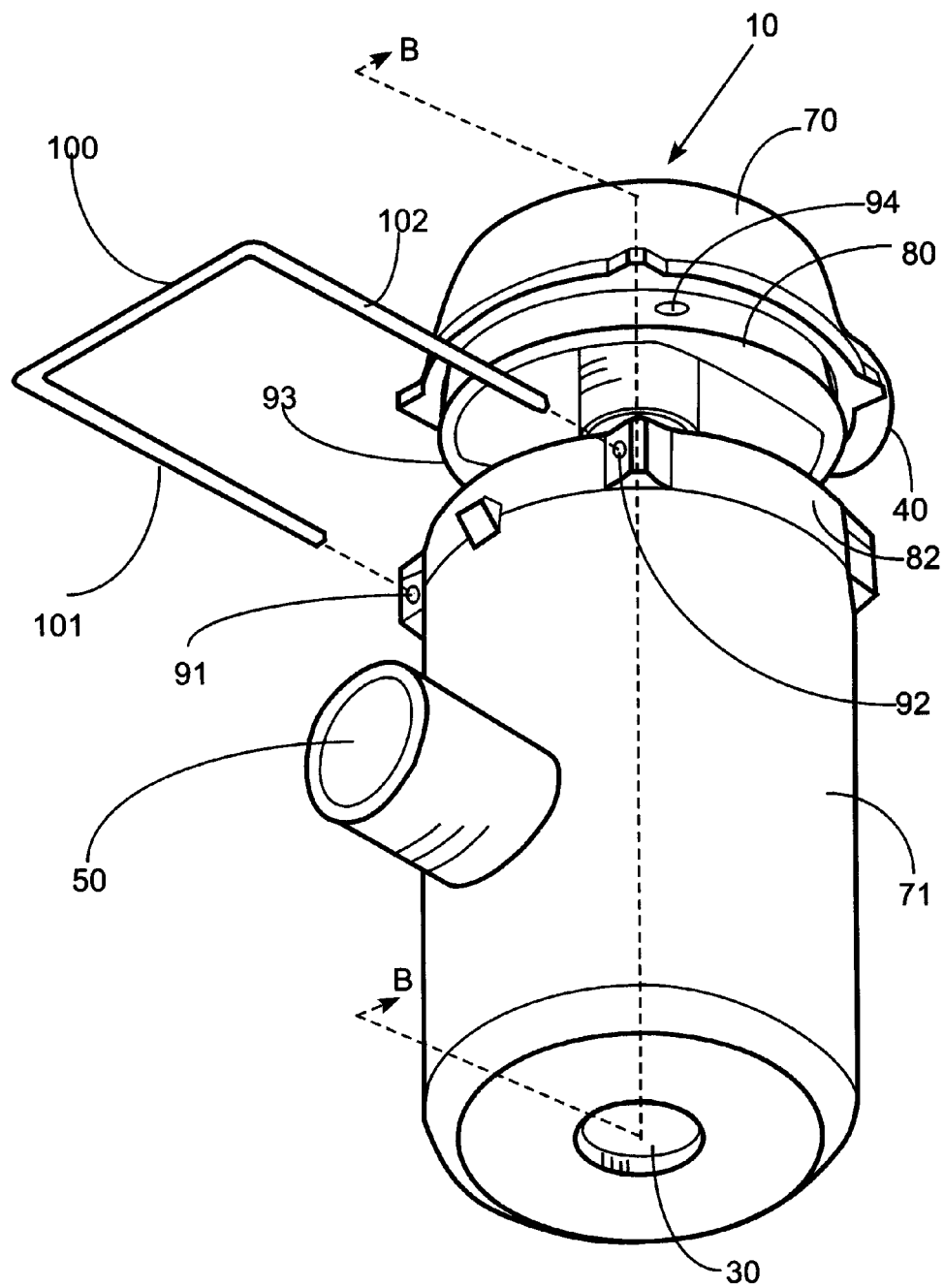
FIG. 4 is a bottom perspective "exploded" view of the gas trap of the present invention, showing a preferred embodiment employing a "U" shaped member as a component of the quick-release means for releasably securing the bottom member of the gas trap to the top member.

As may be best seen from FIG. 4, apertures 91, 92 are provided in bottom member 71, and similar-sized apertures 93, 94 are provided in top member 70, each of apertures 91, 92 in bottom member 71 and apertures 93, 94 in top member 70 adapted to respectively frictionally receive therewithin respective elongate arms 101, 102 of quick release means 100, so as to permit securement of bottom member 71 to top member 70.

Figure 6A:
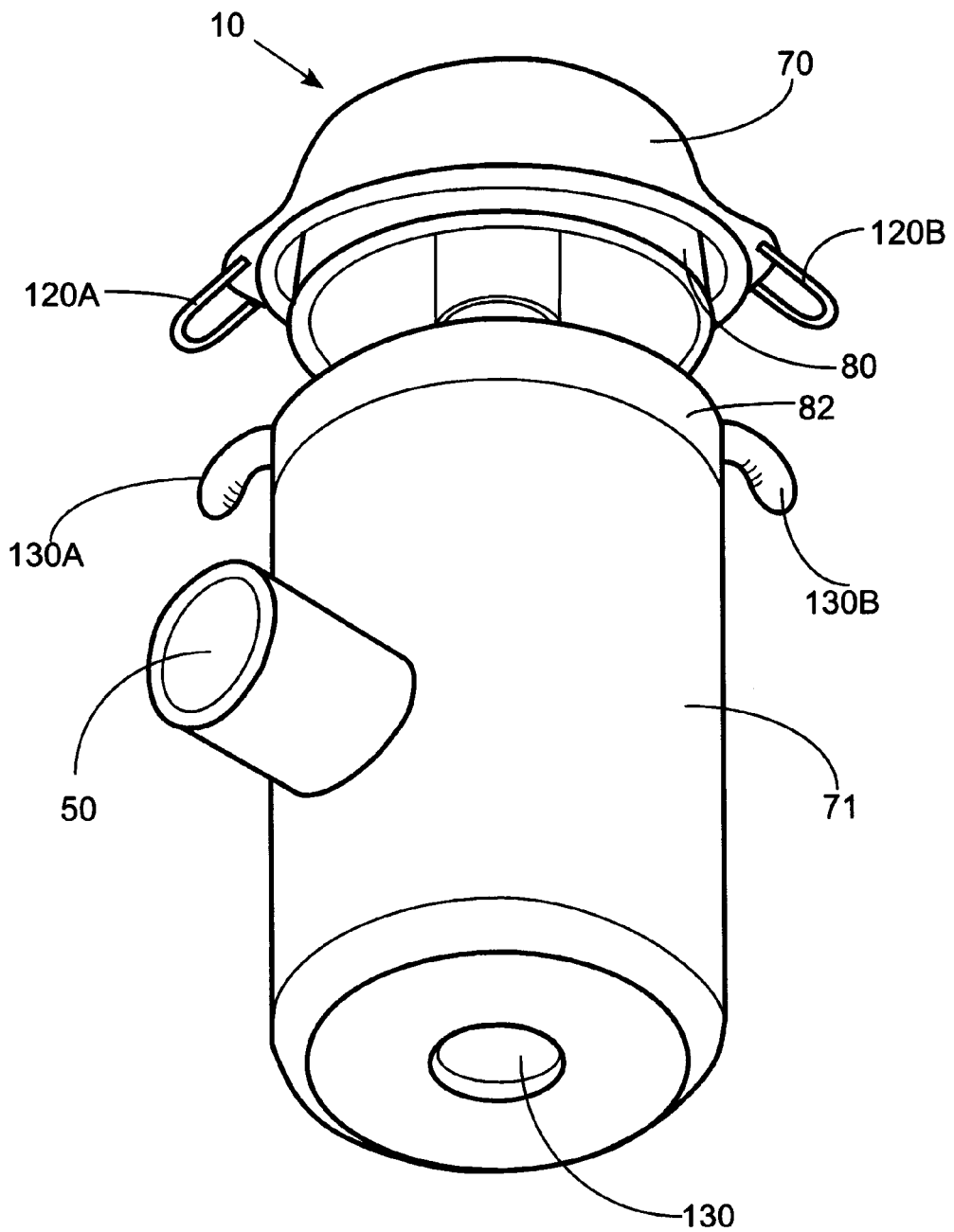
FIG. 6a is an bottom perspective "exploded" view of the gas trap of the present invention, utilizing another form of quick release means.

FIG. 6A shows a bottom perspective view of the gas trap 10 of the present invention, showing an alternative configuration for the quick release means 100 of the present invention, which in the embodiment shown comprises a plurality of bale members 120a, 120b affixed about the lower portion of top member 70, and a corresponding plurality of protuberances 130a, 130b disposed about the periphery of the upper portion 82 of bottom member 71 which are each adapted to matingly engage bale members 120a, 120b, so as to permit releasable securement of top member 70 to bottom member 71.

Figure 6B:
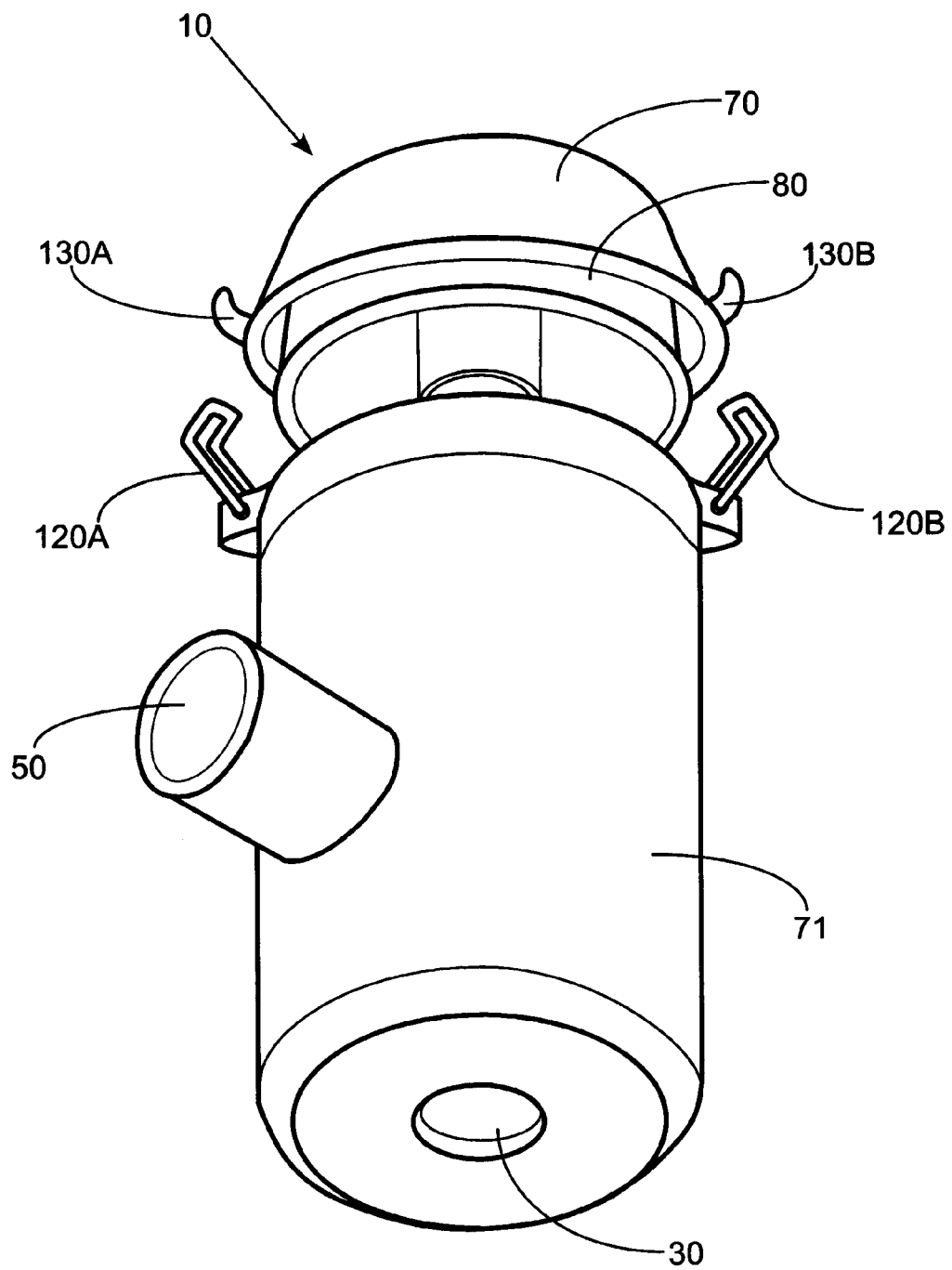

FIG. 6b shows a similar bottom perspective view of a modified version of the gas trap 10 of the present invention shown in FIG. 6a, wherein the plurality of bale members 120a, 120b are instead affixed about the periphery of the upper portion of bottom member 71, and a corresponding plurality of protuberances 130a, 130b disposed about the periphery of the lower portion of top member 70 are provided. Protuberances 130a, 130b are each adapted to matingly engage bale members 120a, 120b so as to permit releasable securement of top member 70 to bottom member 71.

Figure 7:
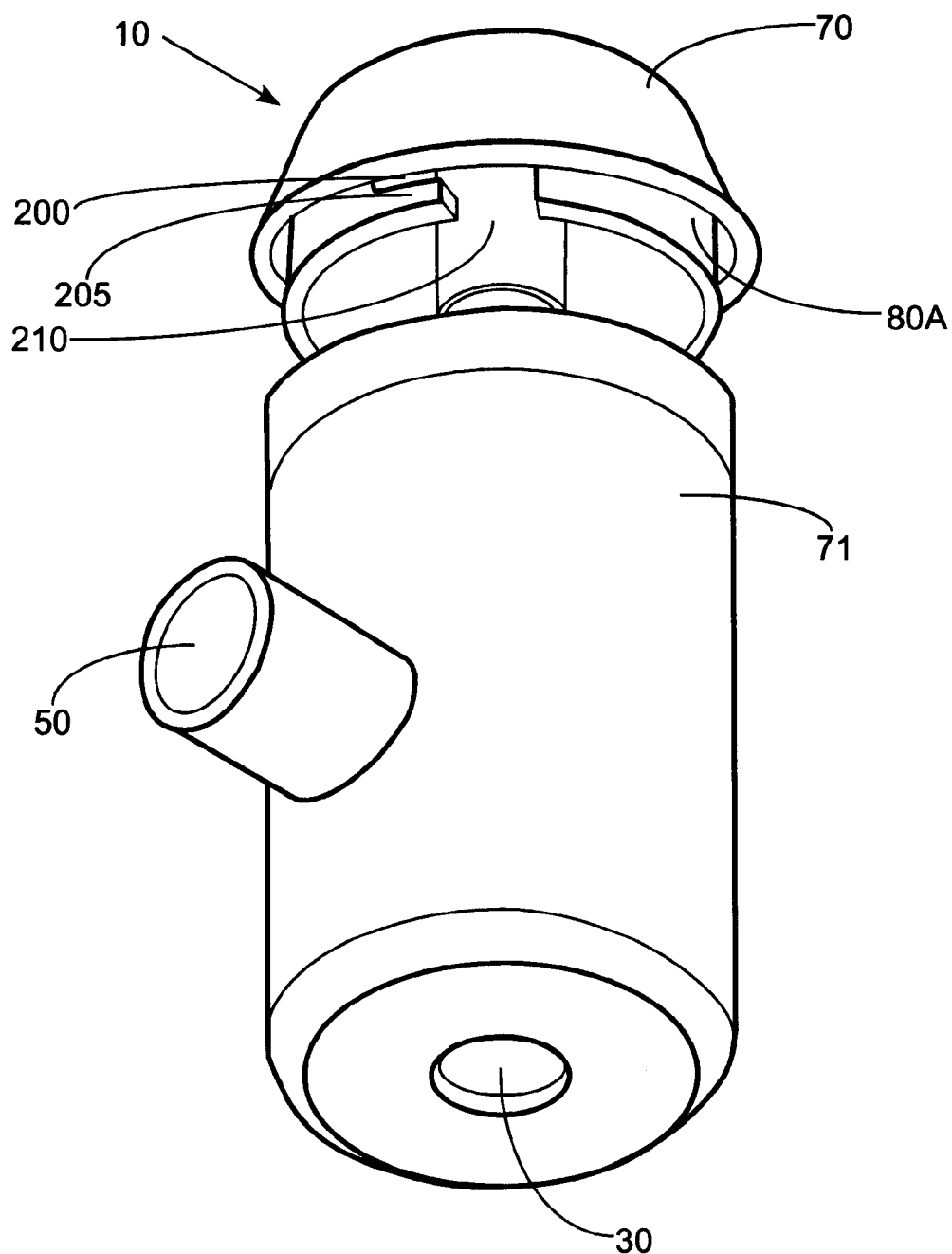
FIG. 7 is an bottom perspective "exploded" view of the gas trap of the present invention, showing a further variation of the quick release means contemplated for use in this invention, using a segmented rim on each of mating surfaces on the lower portion of the top member (shown) and a similar corresponding segmented rim on the upper portion of the bottom member (not shown).

FIG. 7 shows a bottom perspective view of the gas trap 10 of the present invention, showing a still further alternative configuration for the quick release means 100 of the present invention, which in the embodiment shown comprises a segmented ring 80a on top member 70, having a cavity or groove 200 and a retaining element 205. A similar segmented ring 80b (not shown) is disposed on bottom member 71, having a retaining element 206 (not shown but similar to retaining element 205) which, upon fittingly securing bottom member 71 to top member 70, may be inserted within segmented portion 210 in top member 70 and upon rotation of bottom member 71 relative to top member 70 retaining element 206 is directed within cavity 205, thereby preventing removal of bottom member 71 from top member 70. Detachment of bottom member 71 from top member 70 in this particular quick-release embodiment is simply accomplished by rotation of bottom member 70 in an opposite direction so as to remove retaining element 206 from groove 200, and lowering/removing bottom member 71 when retaining element 206 is thereby permitted to move from within groove 205 and pass within segmented portion 210.

Although the disclosure describes and illustrates preferred embodiments of the invention, it is to be understood that the invention is not limited to these particular embodiments.

Many variations and modifications will now occur to those skilled in the art.

For a complete definition of the invention and its intended scope, reference is to be made to the summary of the invention and the appended claims read together with and considered with the disclosure and drawings herein.

We claim:

1. A gas trap apparatus for liberating gas from drilling mud, comprising: an elongate, vertically-downwardly extending shaft, having stirring means thereon to stimulate and cause circulation of drilling mud when extended into and rotated within drilling mud; motor means for rotating said downwardly-extending shaft, a top member, situated below said motor means, said shaft passing vertically downwardly through and extending below said top member, having a gas collection port in said top member for allowing gas liberated from said drilling mud to be collected and withdrawn for analysis; a bottom member extending around said shaft; and quick-release coupling means, releasably coupling said upper portion of said bottom member to said lower portion of said top member to permit rapid detachment of said bottom member from said top member to thereby allow access to said downwardly-extending shaft and stirring means for servicing or replacement said quick release coupling means comprising a "U" shaped locking member removably insertable into apertures in each of said top member and said bottom member.

2. The gas trap apparatus as claimed in claim 1, wherein said quick-release coupling means comprises at least one manually-actuated clip which may be easily released to permit detachment of said upper portion of said bottom section from said lower portion of said top section.

3. The gas trap apparatus as claimed in claim 2, wherein said at least one manually-actuated clip comprises: (i) a plurality of bale members, pivotally secured to said lower portion of said top section about a periphery thereof, and (ii) a plurality of protuberances, extending from said upper portion of said bottom member, engageable with said bale members to releasably secure said bottom member to said top member.

4. The gas trap apparatus as claimed in claim 2, wherein said at least one manually-actuated clip comprises: (i) a plurality of bale members, pivotally secured to said upper portion of said bottom section about a periphery thereof, and (ii) a plurality of protuberances, extending from said bottom portion of said top member, engageable with said bale members to releasably secure said bottom member to said top member.

5. The gas trap apparatus as claimed in claim 1, wherein said quick-release coupling means comprises segmented rim means on each of said lower portion of said top member and said upper portion of said bottom member, to permit locked engagement thereof, wherein said upper portion of said bottom member when inserted into and rotated in a first direction about a vertical axis relative to said top member, becomes secured to said top member due to engagement of said respective segmented rim means, and when said bottom member is rotated in an opposite direction about said vertical axis said bottom member may be removed from engagement with said top member.

6. A gas trap apparatus for liberating gas from drilling mud, comprising: an elongate, vertically-downwardly extending rotatable shaft, having radially outwardly-extending bar members adapted when extended into drilling mud and rotated therein to cause stirring of said drilling mud and liberation of gas therefrom; motor means for rotating said downwardly-extending shaft; a top member situated below said motor means, said shaft passing vertically downwardly through and extending below said top member; a gas collection port in said top member for allowing gas liberated from said drilling mud to be collected for analysis; a bottom member extending around said shaft, having a mud ingress aperture therein and a mud egress aperture therein, and quick-release coupling means, releasably coupling said upper portion of said bottom member to said lower portion of said top member to permit rapid detachment of said bottom member from said top member to thereby allow access to said downwardly-extending shaft and stirring means for servicing or replacement said quick release coupling means comprising a "U" shaped locking member, which is removably insertable into apertures in each of said top member and said bottom member.

* * * * *